United States Patent
Pederson

(10) Patent No.: US 7,167,746 B2
(45) Date of Patent: Jan. 23, 2007

(54) ANTI-COAGULATION AND DEMINERALIZATION SYSTEM FOR CONDUCTIVE MEDICAL DEVICES

(75) Inventor: Brian D. Pederson, Andover, MN (US)

(73) Assignee: ATS Medical, Inc., Plymouth, MN (US)

( * ) Notice: Subject to any disclaimer, the term of this patent is extended or adjusted under 35 U.S.C. 154(b) by 41 days.

(21) Appl. No.: 10/889,328

(22) Filed: Jul. 12, 2004

(65) Prior Publication Data
US 2006/0009804 A1 Jan. 12, 2006

(51) Int. Cl.
*A61N 1/00* (2006.01)

(52) U.S. Cl. .......................................... 607/2

(58) Field of Classification Search ................. 607/116, 607/62, 1, 2, 9, 50, 115; 604/507
See application file for complete search history.

(56) References Cited

U.S. PATENT DOCUMENTS

| | | |
|---|---|---|
| 3,579,645 A | 5/1971 | Bokros |
| 3,726,762 A | 4/1973 | Puharich |
| 4,008,710 A | 2/1977 | Chmiel |
| 4,038,702 A | 8/1977 | Sawyer |
| 4,600,405 A | 7/1986 | Zibelin |
| 4,753,652 A | 6/1988 | Langer et al. |
| 4,769,032 A | 9/1988 | Steinberg |
| 4,979,955 A | 12/1990 | Smith |
| 5,135,538 A | 8/1992 | Pawlak et al. |
| 5,443,446 A | 8/1995 | Shturman |
| 5,487,760 A | 1/1996 | Villafana |
| 5,530,355 A | 6/1996 | Doty |
| 5,603,731 A | 2/1997 | Whitney |
| 5,800,536 A | 9/1998 | Fisher et al. |
| 5,810,015 A | 9/1998 | Flaherty |
| 5,853,005 A | 12/1998 | Scanlon |
| 5,869,189 A | 2/1999 | Hagood, IV et al. |
| 5,919,223 A | 7/1999 | Goldfarb |
| 5,928,224 A | 7/1999 | Laufer |
| 5,944,751 A | 8/1999 | Laub |
| 5,954,058 A | 9/1999 | Flaherty |
| 6,047,700 A | 4/2000 | Eggers et al. |
| 6,083,219 A | 7/2000 | Laufer |
| 6,143,035 A | 11/2000 | McDowell |
| 6,152,955 A | 11/2000 | KenKnight et al. |
| 6,201,991 B1 | 3/2001 | Chekanov |
| 6,394,096 B1 | 5/2002 | Constantz |
| 6,463,323 B1 | 10/2002 | Conrad-Vlasak et al. |
| 6,505,080 B1 | 1/2003 | Sutton |
| 6,534,538 B2 | 3/2003 | Rajamannan |
| 6,551,990 B2 | 4/2003 | Giachelli et al. |
| 6,556,872 B2 | 4/2003 | Hauck |
| 6,560,489 B2 | 5/2003 | Hauck |
| 2002/0169480 A1 | 11/2002 | Zhu et al. |
| 2003/0093124 A1 | 5/2003 | Sutton |

*Primary Examiner*—Scott M. Getzow
(74) *Attorney, Agent, or Firm*—Haugen Law Firm PLLP

(57) ABSTRACT

A system for minimizing and/or eliminating coagulative or mineral deposits on respective blood-contacting surfaces of implanted medical devices includes an implantable system having a current generating device that is electrically coupled to at least first and second electrodes for developing a current therebetween. The at least first and second electrodes are disposed across a patient's thoracic cavity in a manner so that a particular implanted medical device having at least a portion thereof that is fabricated from an electrically conductive material is disposed in a path substantially between such electrodes, thereby focusing the generated electrical current at the electrically conductive portion of the implanted medical device for therapeutic treatment thereat.

9 Claims, 4 Drawing Sheets

ANTI-COAGULATION AND DEMINERALIZATION SYSTEM FOR CONDUCTIVE MEDICAL DEVICES

FIELD OF THE INVENTION

The present invention relates to systems and methods for preventing coagulation and/or mineralization build-up on implanted medical devices generally, and more particularly to the focused application of electrical current at electrically conductive portions of implanted medical devices for preventing such coagulation and mineralization build-up at such electrically conductive portions.

BACKGROUND OF THE INVENTION

Implantable biomedical devices are gaining widespread acceptance in the medical industry, and are finding increasing applicability as permanent solutions to medical problems. What at one time represented last-resort options in treating medical maladies such as defective or diseased coronary valves in the human vasculature have now become primary care procedures. The success of implantable medical devices, and particularly prosthetic devices in coronary-related procedures has lead to research and implementation of other applications of implantable prosthetic medical devices for addressing a wide variety of medical issues.

As medical device implantation procedures become more commonplace, and physicians' confidence in the long-term reliability of such implanted devices expands, such medical devices are being implanted in patients who are expected to live many years subsequent to the implantation procedure. Accordingly, an ever-increasing pool of prospective patients is being created as candidates for medical device implantation. As a result, the implanted medical devices are being expected to operate properly for an extended period of time.

An issue that arises as such medical devices are being utilized in vivo for relatively long periods of time is the biological effects on the performance of such devices. In particular, the formation of deposits such as coagulative blood components and/or blood-borne minerals on blood-contacting surfaces of the implanted medical devices is a major source of performance diminishment and/or device failure.

A particular example of such biological effects on an implanted medical device is in the specific application of implanted replacement heart valves. Build-up of coagulative blood and/or mineral deposits on such implanted heart valves, and particularly at the valve leaflets thereof, reduce the effectiveness of the heart valves, and may even lead to operational failure thereof.

In the case of mechanical heart valves, implanted device recipients must take anti-coagulation drugs for the remainder of their lives from the time that the device is implanted in order to prevent build-up on respective surfaces of the implanted device. Not only is such a practice inconvenient and expensive, it may also present dangers to the patient wherein the healthy coagulative properties of the patient's blood are suppressed. Such suppression of the normal properties of the patient's blood can lead to excessive bleeding as a result of internal or external injury.

Some systems developed to date utilize electrical energy applied to the implanted medical device to eliminate and otherwise thwart the formation of mineral deposits on respective surfaces thereof. The systems proposed to date, however, utilize electrodes placed on or adjacent to the treatment area (often times the heart, or portions thereof) that are configured to produce an electric charge at the targeted therapy location to minimize or eliminate blood component deposits formed thereon. Because the electrical energy intensity required in achieving such a result is more than nominal, great caution must be taken in order to avoid electrical interference with the normal operation of the heart. Accordingly, many known systems utilize complex sensing and timing arrangements for applying electrical energy to a targeted therapy location only during non-critical periods of the heart beat. In addition, such systems require the positioning of the associated electrodes at locations adjacent to the therapeutic target, which typically means positioning such electrodes at or within certain ventricles of the heart. The electrode implantation procedure alone, therefore, presents its own dangers to the patient.

It is therefore a principal object of the present invention to provide an implantable apparatus which develops and focuses electrical current at an implanted medical device for the minimization and/or elimination of the blood component deposits thereon without having to position current-transmitting electrodes at sensitive regions within the patient's heart.

It is a further object of the preset invention to provide a system for minimizing and/or eliminating deposits on respective blood-contacting surfaces of implanted bio-medical devices by focusing sub-threshold electrical current at electrically conductive portions of the implanted medical device.

SUMMARY OF THE INVENTION

By means of the present invention, the prevention and/or elimination of blood component deposits, such as blood cells, calcium, and the like on blood-contacting surfaces of implanted bio-medical devices is enabled through the imposition of electrical current at such blood-contacting surfaces via remotely-positioned electrodes that are electrically coupled to a current-generating device. The anti-coagulation and demineralization system of the present invention utilizes two or more electrodes spaced-apart and subcutaneously disposed across and about a patient's thoracic cavity. The electrodes respectively send and receive electrical current therebetween, and operate in combination with an implanted bio-medical device disposed within an electric field defined substantially between such electrodes. The implanted bio-medical device is at least partially fabricated from a relatively highly electrically conductive material (as compared to the conductivity of human tissue), such that the electrical field is focused thereat.

Therefore, in combination with an implanted bio-medical device having a blood-contacting portion that is fabricated from an electrically conductive material, an implantable system of the present invention includes a current generating means, a first electrode that is electrically coupled to the current generating means and disposed subcutaneously at a first position external to the patient's thoracic cavity, and a second electrode that is electrically coupled to the current generating means and disposed subcutaneously at a second position external to the patient's thoracic cavity. The second position is preferably spaced from the first position, such that the implanted bio-medical device is operably disposed in a thoracic area substantially between the first and second electrodes. The current generating means accordingly generates a current or electrical field that extends between the first and second electrodes, thereby focusing such current at the blood-contacting portion of the implanted bio-medical device.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
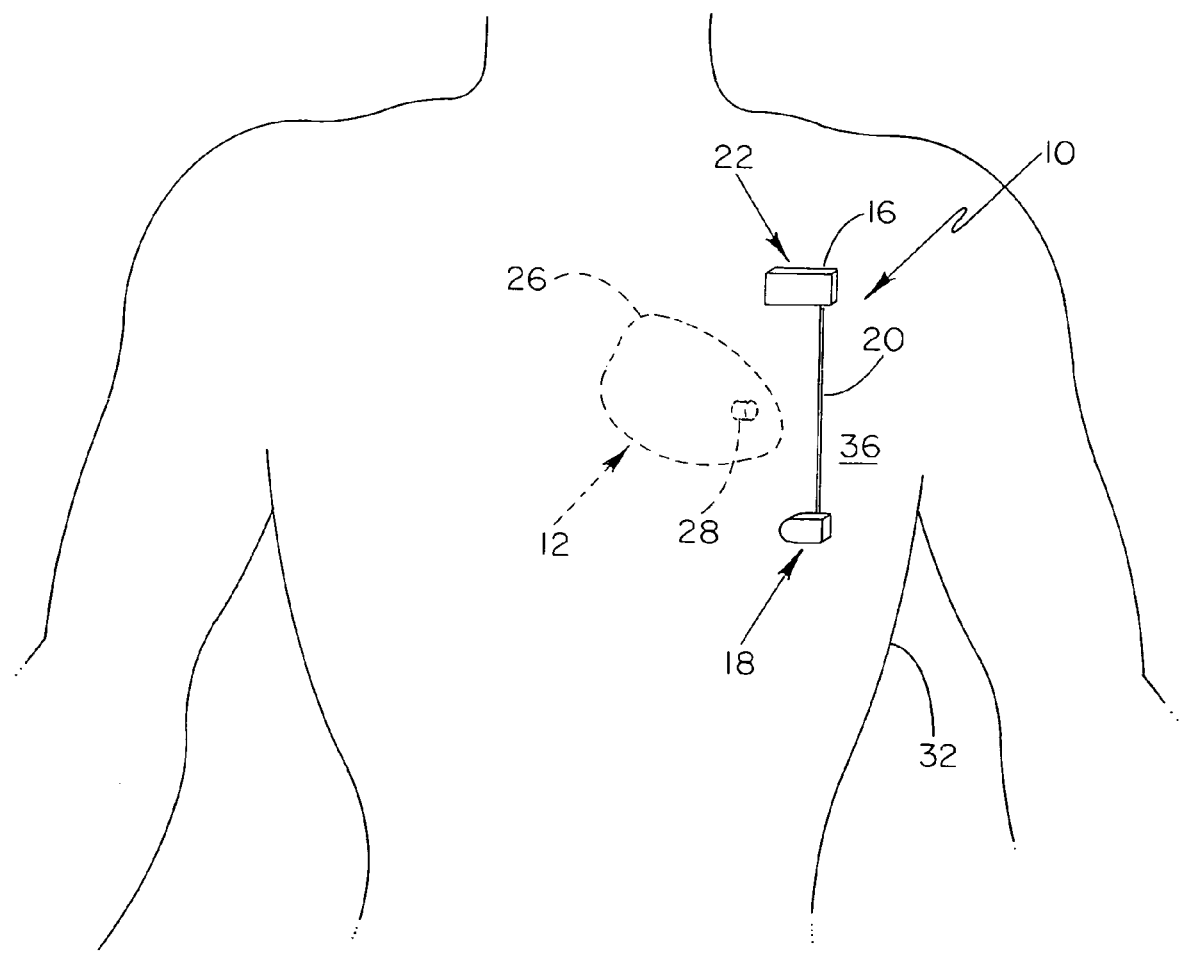
FIG. 1 shows a patient into which the system of the present invention has been operably implanted.

With reference now to the drawings, and first to FIG. 1, an implantable system 10 is shown in a subcutaneous implanted position external to the thoracic cavity 12 of a human patient. Implantable system 10 preferably includes a current generating means 16, a first electrode 18 electrically coupled to current generating means 16 via electrical conduit wire 20, and a second electrode 22 electrically coupled to current generating means 16. Further depicted in FIG. 1 is the patient's heart 26 having a bio-medical device such as a prosthetic heart valve 28 implanted thereat.

As depicted in FIG. 1, first and second electrodes 18, 22 are preferably positioned subcutaneously in the human patient across thoracic cavity 12, and preferably subcutaneously along first side 32 of thoracic cavity 12. In addition, first and second electrodes 18, 22 are preferably specifically positioned so as to substantially bracket prosthetic valve 28 therebetween. Specifically, each of first and second electrodes 18, 22 are positioned such that prosthetic valve 28 is disposed substantially within an electric field extending therebetween. Such a positioning is shown in FIG. 1 by field 36 disposed substantially between first and second electrodes 18, 22.

In operation, current generating means 16 generates a current that is directed through electrical conduit wire 20 to first electrode 18, wherein a closed-loop circuit is enabled by current being passed from first electrode 18 to second electrode 22 through field 36. In this case, the magnitude of current delivered across field 36 is at least sufficient to have a therapeutic effect on electrically conductive portions of prosthetic valve 28. Such a therapeutic effect includes, for example, reducing and or eliminating the existence of coagulative and/or mineralization blood components from respective blood-contacting surfaces of prosthetic valve 28.

In certain embodiments, current generating means 16 provides a 1–2 mA current in a pulsatile mode of delivery. In other embodiments, such current may be provided in a continuous format. The American Medical Institution Guidelines provide that current amperage can be safely applied in a sub-threshold manner through the thoracic cavity by the following relationship; for every 1 kHz increase in frequency, current may be increased by 10 μA. Thus, the current applied in the present invention may be adjusted as desired in both amplitude and frequency, so long as it remains either at a sub-threshold level as described above, or is applied at predetermined time intervals so as not to interfere with the normal cardiac cycle. In addition, such current may be provided in sinusoidal or triangular wave forms, as well as a variety of other continuous and/or discontinuous modes.

In embodiments wherein the current is applied at predetermined time intervals so as not to interfere with the normal cardiac cycle, sensing and control means are incorporated into the system of the present invention. In order to continuously monitor the cardiac cycle for applying electrical energy within the thoracic cavity only during non-critical time periods, sensing means such as conventional sensing amplifiers may be connected to first and second electrodes 18, 22 so as to electrically sense cardiac rhythms and myo potentials. The sensing means delivers responsive electrical signals to a controlling means such as a controlling circuit to indicate when a pre-defined cardiac event, such as a depolarization, is underway. Since the controller means is operably coupled to the current generating means 16, reception by the controller means of an electrical signal indicating a pre-defined aspect of cardiac activity initiates the controller means to interrupt and/or prevent the generation of current to first and second electrodes 18, 22 by current generating means 16. Such an interruption and/or prevention is maintained throughout the time period that corresponding signals are being received by the controller means from the sensor means in one or more of first and second electrodes 18, 22. In such a manner, generation of an electric field between first and second electrodes 18, 22 may be automatically controlled to occur only at interval periods between critical cardiac rhythms. In other words, the controller means restricts the current generating means to supply electrical energy only during certain portions of the cardiac cycle.

Preferably, current generating means 16 is a conventional implantable device that is capable of generating electrical output from a stored potential, such as in an internal battery. For example, current generating means 16 may be located within a conventional housing such as that of a cardiac pacemaker. Since conventional pacemaker devices have external housings which are typically fabricated from a biocompatible metal such as titanium, such an outer enclosure itself may act as second electrode 22. In other embodiments, however, a separate electrode having its own lead wire from current generating means 16 may be provided as second electrode 22 instead of the outer housing of current generating means 16. In any event, second electrode 22 is preferably spaced from first electrode 18, with field 36 created therebetween having the effect of inducing current in electrically conductive portion of valve 28.

Preferably, first and second electrodes 18, 22 are implanted subcutaneously at first side 32 of thoracic cavity 12. In embodiments where the implanted biomedical device targeted for treatment by electrical energy passing between first and second electrodes 18, 22 is disposed at or adjacent heart 26, first and second electrodes 18, 22 are preferably positioned just beneath the patient's dermal tissue. In such a manner, at least a portion of field 36 preferably passes through heart 26, thereby exposing bio-medical device, such as mechanical heart valve 28, to electrical current passing between first electrode 18 and second electrode 22. It is contemplated by the present invention to alter the specific positions of first and second electrodes 18, 22 as described above for applications involving implanted bio-medical devices which are not disposed at or adjacent to heart 26. Devices contemplated by the present invention that, in addition to mechanical heart valves, may be targeted by the therapeutic system include, for example, implanted metallic coronary stents, vascular stents, conductive arterial graft segments, and the like that are disposed in a patient's vasculature system or contained within heart 26.

In each of the preferred embodiments, the implanted bio-medical device is positioned within an area disposed generally between first and second electrodes 18, 22 so as to be disposed within field 36. In this fashion, electrical current is conducted through the implanted bio-medical device during the time that current is passing from first electrode 18 to second electrode 22. As described above, such an electrical current is useful in eliminating and/or preventing blood component deposits on respective surfaces of the implanted bio-medical device. In particular, surfaces of implanted bio-medical devices that are exposed to blood flow have the tendency to harbor deposits of minerals and/or other coagulative components carried in the bloodstream in the absence of anti-coagulation medications taken by the patient. Electrical current passing through such surfaces of the implanted bio-medical devices has the effect of inhibiting the formation, and even reducing existing formations, of such deposits. Therefore, creation of electrical current in such blood-contacting portions of implanted bio-medical devices is extremely helpful to the long-term viability of such medical devices.

In the embodiment illustrated in FIG. 1, implanted heart valve 28 is disposed within field 36 between first and second electrodes 18, 22, which results in electrical current being created in such heart valve 28. An important aspect of the present invention is that at least a portion of, for example, implanted heart valve 28 is fabricated from an electrically-conductive material such as pyrolytic carbon.

Figure 2:
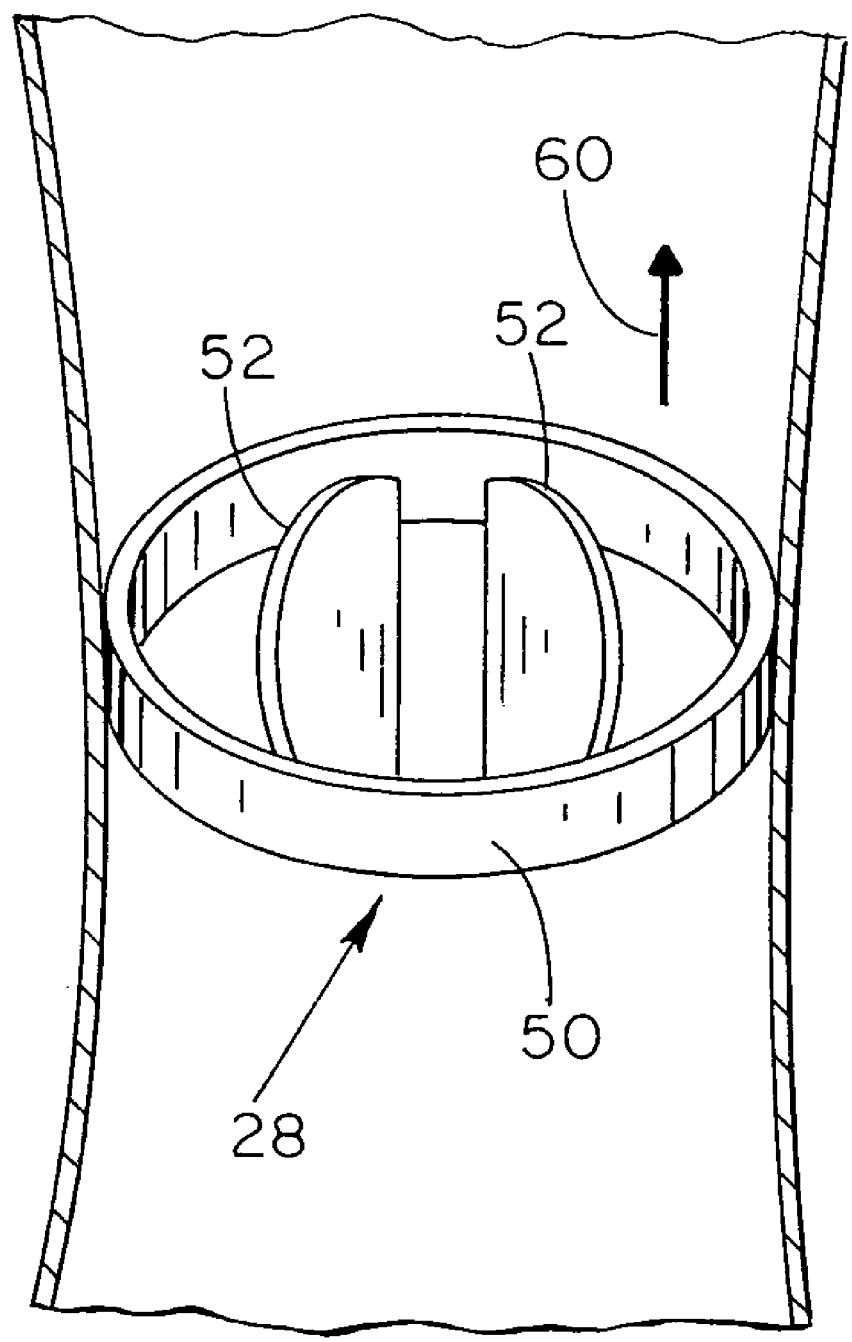
FIG. 2 illustrates a particular example of an implanted bio-medical device of the present invention.

As illustrated in FIG. 2, an example implanted prosthetic heart valve 28 includes a generally cylindrical valve body 50 that is sized and configured to be disposed within the area previously occupied by the native heart valve via sutures or the like. Prosthetic heart valve 28 preferably further includes one or more pivoting valve leaflets 52 secured to valve body 50 by retention mechanisms therewithin. Such valve leaflets 52 pivot from respective open positions, as illustrated in FIG. 2, to respective closed positions to allow blood flow to pass through prosthetic heart valve 28 only in a direction defined by direction arrow 60. Accordingly, valve leaflets 52 and body 50 are directly in the path of the blood flow, and are therefore susceptible to the formation of deposits of coagulative blood elements thereon. Preferably, therefore, at least leaflets 52 and body 50 are fabricated from an electrically conductive material such as pyrolytic carbon so as to effectively focus electrical current passing between first and second electrodes 18, 22 thereat.

The system of the present invention harnesses a basic law of physics, in that electrical current will absolutely follow the path of least electrical resistance between first and second electrodes 18, 22. By incorporating materials into the implantable bio-medical device, such as prosthetic heart valve 28, that are substantially more electrically conductive than the surrounding blood and body tissue, a substantial portion of the electrical current passing between first and second electrodes 18, 22 will be focused at the electrically conductive portions of prosthetic valve 28 so as to accomplish a path of least electrical resistance between first and second electrodes 18, 22. To effectively focus electrical current at respective portions of the implanted bio-medical device, such portions are preferably fabricated from a material that is significantly more electrically conductive than the body tissue and blood that is disposed generally within field 36. Accordingly, such portions of the implanted bio-medical device have an electrical conductivity of at least about 10–100 times that of blood. In other words, the electrically conductive portions of the bio-medical device have a resistance value of less than about 30 Ω·cm. A particularly useful electrically conductive material in such bio-medical devices is pyrolytic carbon which has an electrical resistance value of 0.727 Ω·cm, as compared to blood, which has an electrical resistance value of approximately 300 Ω·cm. Such a low resistance value of the pyrolytic carbon efficiently focuses a significant portion of the electrical current passing between first and second electrodes 18, 22. Accordingly, the overall electrical current being passed between first and second electrodes 18, 22 may be minimized in system 10 of the present invention while still obtaining a desired level of current in designated portions, such as valve leaflets 52 and body 50 of valve 28 to effectively prevent and/or diminish deposits of blood components thereon.

As stated above, a particular aspect of the present invention is in focusing a substantial portion of the electrical current passing between first and second electrodes 18, 22 at desired blood-contacting portions of the implanted bio-medical device 28. As a consequence of such a "focusing" effect, the current generated by current generating means 16 may be correspondingly minimized to a sub-threshold level that does not present dangers to the electrical operation of heart 26, while still providing a sufficient degree of current at electrically conductive portions of device 28 to prevent and/or eliminate coagulative deposits thereon.

A second important aspect of the present invention is in the provision of first and second electrodes 18, 22 being disposed externally of thoracic cavity 12, so as to be substantially spaced from heart 26. Instead, electrodes 18, 22 are preferably positioned at first side 32 of thoracic cavity 12. Electrical impulse systems that require the placement of electrodes on or within critical areas of the patient's body, such as within thoracic cavity 12, or on or within heart 26, themselves present a difficult and dangerous operative procedure. For example, placement of such electrodes within the cavities of heart 26 is an extremely delicate procedure which can result in damage to the heart. It is therefore a significant advantage of the present invention to obtain a desired level of electrical current at, for example valve leaflets 52 and body 50, without the necessity of placing electrodes at or within heart 26. Instead, the present invention provides for the subcutaneous placement of first and second electrodes 18, 22 at positions in which the distance between the electrodes 18, 22 can be minimized, and the current conducted to the surface of the implanted bio-medical device can be optimized. The operative procedure for subcutaneous placement of first and second electrodes 18, 22 at locations external to the thoracic cavity is substantially more simple and less dangerous to the patient than placement of such electrodes adjacent to or within heart 26.

To electrically couple current generating means 16 to first electrode 18, a surgeon may be required to utilize a common tunneling tool to create a subcutaneous path for placement of electrically conductive wire 20 therein. In doing so, the surgeon is able to implant system 10 without entering the thoracic cavity 12. As a result, the system of the present invention may be implanted without serious risks.

In a preferred embodiment of the present invention, first and second electrodes 18, 22 are each positioned adjacent to the innermost layer of the patient's dermal tissue.

As described above, second electrode 22 may be the outer housing itself of current generating means 16, or may instead or additionally be a distinct electrode body electrically coupled to current generating means 16 via a distinct electrically conductive lead wire. Preferably, such separate electrodes may be those commonly utilized in implanted electrical generation devices such as pacemakers and defibrillators. Accordingly, electrodes useful in system 10 of the present invention may be fabricated from, for example, titanium, platinum iridium, stainless steel, and carbon black. Such electrodes may preferably be in the form of screen, solid, and printed pattern type configurations. In preferred embodiments, subcutaneous patch electrodes having a mean diameter of about 8–10 cm are utilized due to the fact that the larger the surface area of the electrode will decrease the current densities, which will be less likely to cause undesired skeletal and/or cardiac muscle stimulation.

Though system 10 of the present invention is preferably implanted, it is contemplated by the present invention that system 10 may instead be utilized externally, as on a belt attachment or similar device, and by adhesively affixing first and second electrodes 18, 22 to respective locations of the patient, with the electrical current between such first and second electrodes maintaining a path substantially within field 36.

Figure 3:
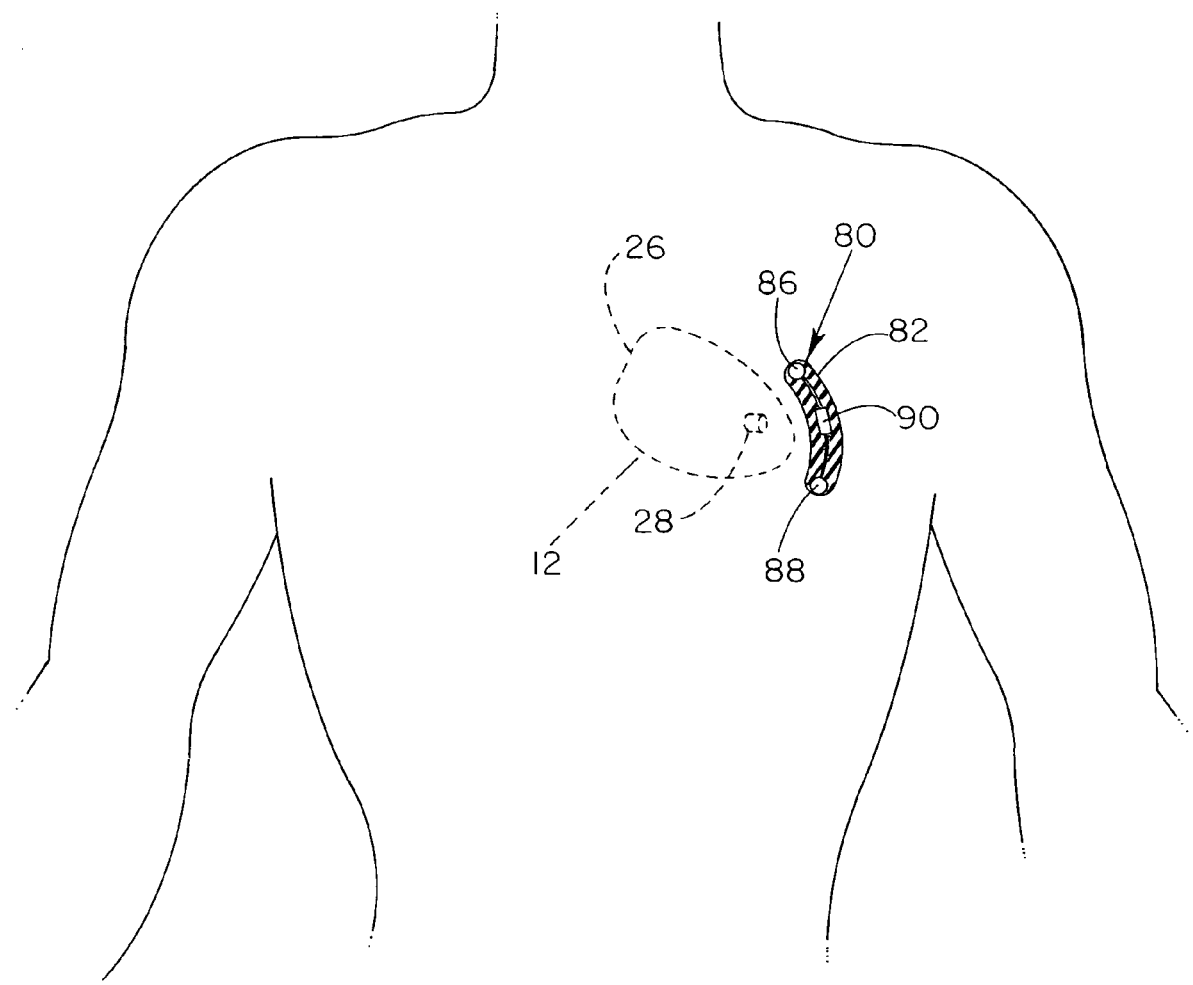
FIG. 3 shows a patient into which a system of the present invention has been operably implanted.

In another embodiment of the present invention, as illustrated in FIG. 3, implantable system 80 preferably includes a monolithic electrical field device 82 that is implantably positioned at a subcutaneous location adjacent to the thoracic cavity and spaced from an implanted medical device such as prosthetic valve 28. Implantable electrical field device 82 preferably includes at least first and second electrodes 86, 88 incorporated therewith, which first and second electrodes 86, 88 are preferably coupled to a current generating device 90, which is preferably integrally formed with electrical field device 82. In other embodiments, however, current generating device 90, which is separate and distinct from electrical field device 82, and is electrically coupled to first and second electrodes 86, 88 via electrically conductive wiring or the like.

Figure 4:
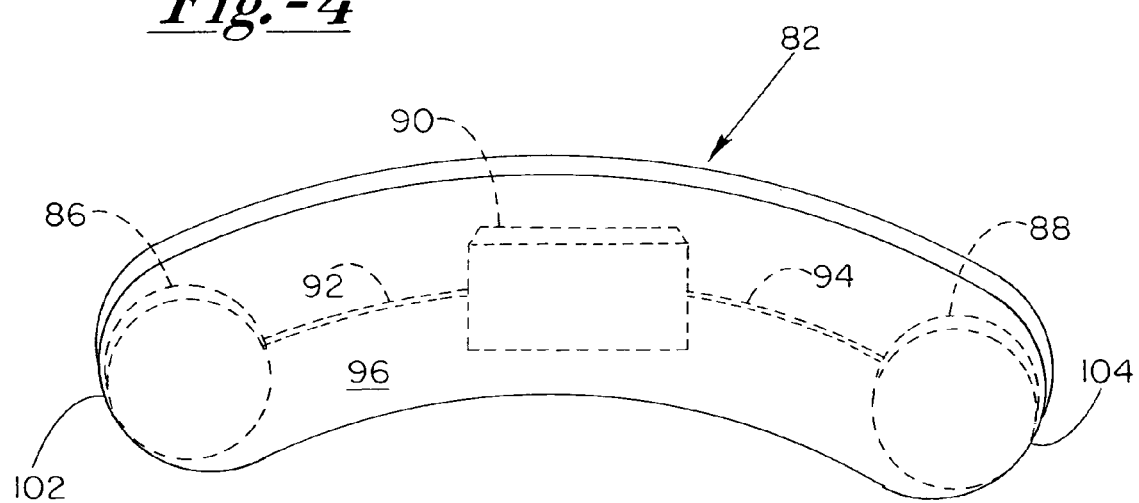
FIG. 4 illustrates an isolation view of the implantable system illustrated in FIG. 3.

As illustrated in the isolation view of FIG. 4, electrical field device 82 preferably incorporates a body 96 that is fabricated from a relatively flexible bio-compatible material such as polyurethane or silicon rubber. First and second electrodes 86, 88 may be disposed on an outer surface of, or within body 96. Likewise, current generating device 90 may also be selectively disposed on an outer surface or within body 96 of electrical field device 82. As illustrated in FIG. 4, electrical wiring leads 92, 94 preferably electrically connect one or more of first and second electrodes 86, 88 to current generating device 90. In still further embodiments of the invention, one of such first and second electrodes 86, 88 may comprise the outer housing of current generating device 90, as described above. In such an embodiment, only a single electrically conductive lead 92 is required to electrically couple a combined current generating device and first electrode 86 to second electrode 88.

Body 96 of electrical field device 82 is preferably sized and configured to enable the operable and implantable positioning thereof at a convenient distance from the respective implanted bio-medical device such as prosthetic valve 28, while still providing an electric field encompassing valve 28 such than an electrical current may be induced in electrically conductive portions of prosthetic valve 28 when current is being passed between first and second electrodes 86, 88.

The embodiment illustrated in FIGS. 3 and 4 operates on the same principle as that described with reference to FIG. 1, with the exception that first and second electrodes 86, 88 are contained within, or are operably attached to body 96 of electrical field device 82. In order to operably create an electric field that is sufficiently large to encompass targeted implanted bio-medical devices, first and second electrodes 86, 88 are preferably positioned at respective distal ends 102, 104 of body 96. In this way, body 96 may be minimized in overall size to accommodate an electrical field of sufficient dimensions.

In a particular embodiment of the invention, body 96 is preferably about 8–25 cm in length, 0.5–8 cm in width, and 0.1–3 cm in depth, with such dimensions being variable as a result of the flexible nature of the material making up body 96. In such an embodiment, first and second electrodes 86, 88 are preferably at least about 8–10 cm apart from one another so as to establish an electrical field generally disposed therebetween that is sufficiently large in dimension so as to encompass one or more targeted bio-medical devices, such as valve 28.

As illustrated in FIG. 3, electrical field device 82 is preferably in an anterior subclavian position in a subcutaneous pocket so that the electric field generated by device 82 is sufficient so as to encompass heart 26. In addition, electrical field device 82 is further positioned such that the electrical field produced when electrical current is being passed between first and second electrodes 86, 88 encompasses valve 28 so as to operably induce a therapeutic level of current at electrically conductive portions thereof.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method for inhibiting the formation and adherence of blood components on an electrically-conductive blood-contacting portion of an implanted bio-medical device in a human patient, said method comprising:
   (a) providing an implanted system having:
      (i) a current generating means;
      (ii) a first electrode electrically coupled to said current generating means; and
      (iii) a second electrode electrically coupled to said current generating means;
   (b) positioning said first electrode subcutaneously at a first position external to the patient's thoracic cavity;
   (c) positioning said second electrode subcutaneously at a second position external to the patient's thoracic cavity, wherein said second position is spaced from said first position such that the implanted bio-medical device is operably disposed in a thoracic area substantially between said first and second electrodes; and
   (d) causing said current generating means to generate a current that extends between said first and second electrodes, thereby focusing such current at the blood-contacting portion of said implanted bio-medical device.

2. A method as in claim 1 wherein said current generating means is integral and contained within a pacemaker system.

3. A method as in claim 1 wherein said blood-contacting portion of said implanted bio-medical device is fabricated from the group consisting of pyrolytic carbon, titanium, and stainless steel.

4. A method as in claim 1 wherein said implanted bio-medical device is selected from the group consisting of a prosthetic heart valve, a cardiac stent, and an artificial conductive blood vessel.

5. A method as in claim 4 wherein said blood-contacting portion of said prosthetic heart valve is the valve housing and valve leaflets thereof.

6. A method as in claim 1 wherein the generated current is subthreshold.

7. A method as in claim 1 wherein said first and second electrodes are secured to an implantable monolithic structure that is operably implanted at a subcutaneous position.

8. A method as in claim 7 wherein said current generating means is disposed at said monolithic structure.

9. A method for inhibiting the formation and adherence of blood components on an electrically-conductive blood-contacting portion of an implanted bio-medical device in a human patient, said method comprising:
(a) providing a therapeutic system having:
  (i) a current generating means;
  (ii) a first electrode electrically coupled to said current generating means; and
  (iii) a second electrode electrically coupled to said current generating means;
(b) removably securing said first electrode to a first position external to the patient's body;
(c) removably securing said second electrode to a second position external to the patient's body, wherein said second position is spaced from said first position such that the implanted bio-medical device is operably disposed in a thoracic area substantially between said first and second electrodes; and
(d) causing said current generating means to generate a current that extends between said first and second electrodes, thereby focusing such current at the blood-contacting portion of said implanted biomedical device.

* * * * *